(12) United States Patent
Parker

(10) Patent No.: US 8,187,396 B2
(45) Date of Patent: May 29, 2012

(54) METHOD OF MAKING A SELF-EXPANDING STENT

(75) Inventor: Fred T. Parker, Unionville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 441 days.

(21) Appl. No.: 12/481,362

(22) Filed: Jun. 9, 2009

(65) Prior Publication Data
US 2009/0309273 A1 Dec. 17, 2009

Related U.S. Application Data

(60) Provisional application No. 61/061,003, filed on Jun. 12, 2008.

(51) Int. Cl.
C22F 1/10 (2006.01)
(52) U.S. Cl. .......... 148/563; 148/676; 623/1.18
(58) Field of Classification Search .......... None
See application file for complete search history.

(56) References Cited

U.S. PATENT DOCUMENTS

| | | | |
|---|---|---|---|
| 5,540,712 A * | 7/1996 | Kleshinski et al. | 623/1.19 |
| 5,607,445 A | 3/1997 | Summers | |
| 6,042,606 A * | 3/2000 | Frantzen | 623/1.18 |
| 6,336,937 B1 | 1/2002 | Vonesh et al. | |
| 6,416,544 B2 | 7/2002 | Sugita et al. | |
| 7,214,240 B2 | 5/2007 | Bonsignore et al. | |
| 2003/0083732 A1 | 5/2003 | Stinson | |
| 2004/0236409 A1 | 11/2004 | Pelton et al. | |

OTHER PUBLICATIONS

Brochure: "Medical Balloons," *Advanced Polymers Incorporated*, Salem NH, www.advpoly.com, Publicly available prior to Jun. 12, 2008, 2 pages.

* cited by examiner

*Primary Examiner* — George Wyszomierski
(74) *Attorney, Agent, or Firm* — Brinks Hofer Gilson & Lione

(57) ABSTRACT

A method of making a self-expanding stent includes disposing a stent comprising a shape memory alloy about an inflatable body, and applying a coolant to a surface of the stent. The inflatable body is inflated to radially expand the stent to an expanded diameter from an initial diameter, and the coolant is reapplied to the surface of the stent. The inflatable body is deflated, and the stent is positioned about a mandrel sized to accommodate the expanded diameter of the stent, where the stent reaches a mandrel-defined diameter. The stent is heat set at the mandrel-defined diameter so as to impart a memory of an expanded configuration of the stent to the shape memory alloy.

20 Claims, 5 Drawing Sheets

METHOD OF MAKING A SELF-EXPANDING STENT

RELATED APPLICATION

The present patent document claims the benefit of the filing date under 35 U.S.C. §119(e) of U.S. Provisional Patent Application Ser. No. 61/061,003, which was filed on Jun. 12, 2008, and is hereby incorporated by reference in its entirety.

TECHNICAL FIELD

The present disclosure relates generally to methods of manufacturing medical devices and more particularly to methods of manufacturing stents.

BACKGROUND

Stents are tubular support structures that may be implanted into body vessels to treat blockages, occlusions, narrowing ailments and other problems that may restrict flow through the vessel. Numerous vessels throughout the vascular system, including peripheral arteries, such as the carotid, brachial, renal, iliac and femoral arteries, and other vessels, may benefit from treatment by a stent.

Stents generally comprise a framework of interconnected struts that allow the stent to be collapsed into a low profile configuration for delivery and then radially expanded at the treatment site to contact the vessel wall. Balloon-expandable stents expand in response to the inflation of a balloon, whereas self-expanding stents deploy automatically when released from a delivery device.

Self-expanding stents are often fabricated from superelastic or shape memory alloys, such as Nitinol, which can "remember" and recover a previous shape. For example, a self-expanding stent made of a shape memory alloy may be trained to have a memory of an expanded configuration which it recovers after passing through the vessel in a compressed, low profile state. In the case of Nitinol alloys, the source of the shape recovery is a phase transformation between a lower temperature phase (martensite) and a higher temperature phase (austenite) that may be driven by an increase in temperature (shape memory effect) or by the removal of an applied stress (superelastic effect).

The process of training a stent made of a Nitinol alloy to have a particular remembered shape generally includes heat setting the stent while it is constrained in the configuration of interest. For example, a laser-cut stent may be disposed about a mandrel having an outer diameter corresponding to the desired inner diameter of the expanded stent, and then heated at a temperature appropriate to "set" the desired expanded shape. To facilitate positioning the stent about the mandrel for heat setting, a tapered mandrel may be employed to provide for a gradual radial expansion of the stent. To further aid the expansion, the stent may be cooled (e.g., by spraying a coolant onto the stent) so as to transform the Nitinol alloy to the low temperature martensitic phase, which is more readily deformed than austenite. As the cooled stent is advanced over the tapered mandrel, however, portions of the strut framework can experience high stresses that may result in strut misalignments. After the stent is disposed on the larger diameter of the mandrel, a tedious process of reorienting misaligned struts may be necessary before the stent undergoes the heat setting treatment to set the expanded shape.

BRIEF SUMMARY

A new method of making a self-expanding stent is described herein. The method allows a stent comprising a shape memory alloy to be radially expanded for a heat setting treatment without experiencing excessive longitudinal stresses or strut misalignments. Accordingly, the stent may undergo the heat setting treatment without first undergoing a tedious process of reorienting misaligned struts.

According to one embodiment of the method, a stent comprising a shape memory alloy is disposed about an inflatable body and cooled to a temperature sufficient to obtain a martensitic phase of the shape memory alloy in at least a portion of the stent. The inflatable body is inflated to radially expand the stent to an expanded diameter from an initial diameter, and then the inflatable body is deflated. The stent is positioned about a mandrel sized to accommodate the expanded diameter of the stent, where the stent reaches a mandrel-defined diameter, and the stent is heat set at the mandrel-defined diameter so as to impart a memory of an expanded configuration of the stent to the shape memory alloy.

According to a second embodiment of the method, a stent having struts in a regular arrangement and comprising a shape memory alloy is cooled to a temperature sufficient to obtain a martensitic phase of the shape memory alloy in at least a portion of the stent, and then radially expanded to an expanded diameter from an initial diameter without substantially disturbing the regularity of the arrangement of the struts. The stent having the expanded diameter is recooled to the temperature and positioned about a mandrel sized to accommodate the expanded diameter, where the stent reaches a mandrel-defined diameter. The stent is heat set at the mandrel-defined diameter so as to impart a memory of an expanded configuration of the stent to the shape memory alloy.

According to a third embodiment of the method, a stent comprising a shape memory alloy is disposed about an inflatable body, and a coolant is applied to a surface of the stent. The inflatable body is inflated to radially expand the stent to an expanded diameter from an initial diameter, and the coolant is reapplied to the surface of the stent. The inflatable body is deflated, and the stent is positioned about a mandrel sized to accommodate the expanded diameter of the stent, where the stent reaches a mandrel-defined diameter. The stent is heat set at the mandrel-defined diameter so as to impart a memory of an expanded configuration of the stent to the shape memory alloy.

DETAILED DESCRIPTION

Figure 1:
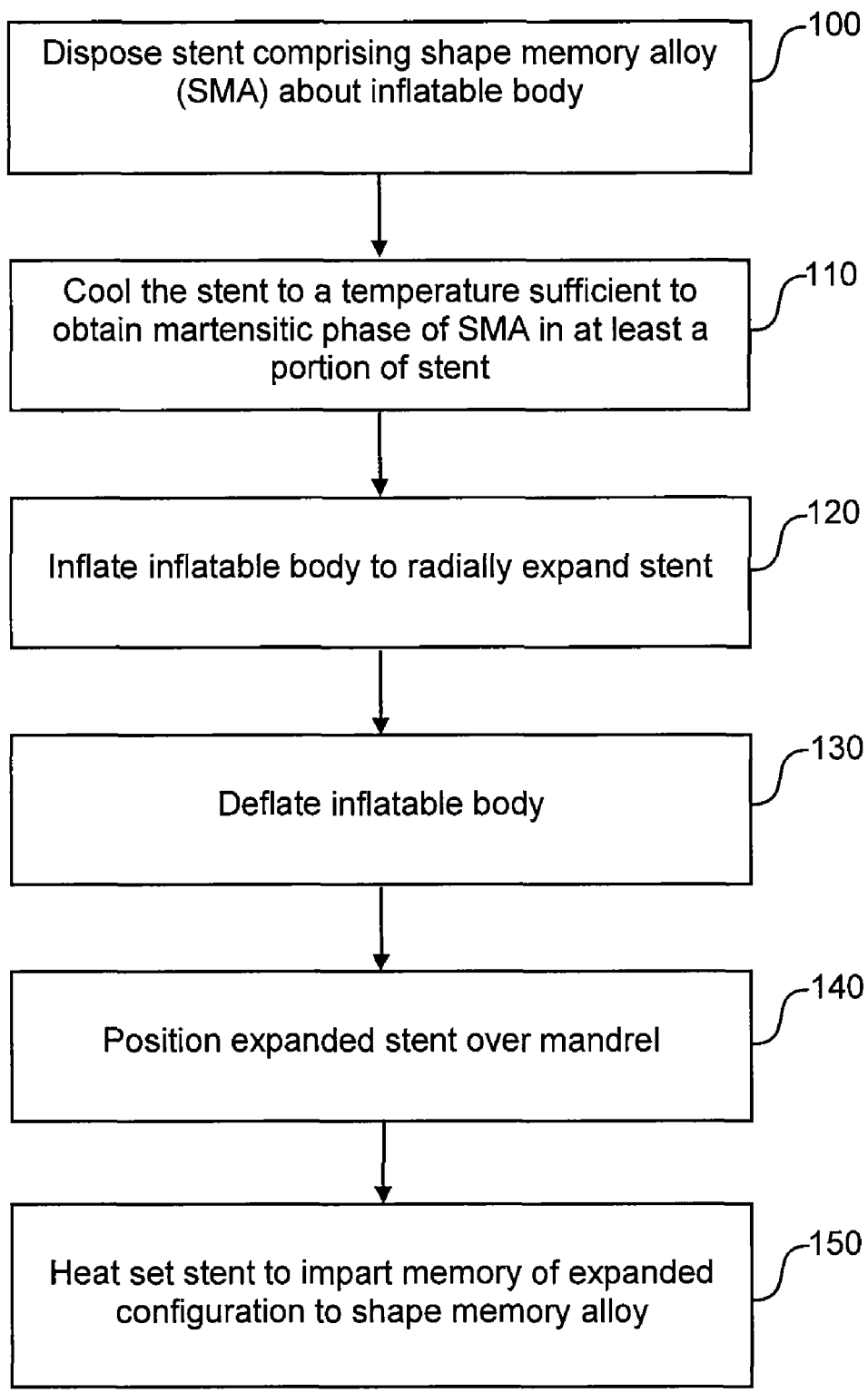
FIG. 1 is a flow chart of the method according to a first embodiment.

A method of expanding a stent comprising a shape memory alloy to an expanded diameter for heat setting is described herein. According to a first embodiment, which is represented in the flow chart of FIG. 1, the method includes disposing 100 a stent comprising a shape memory alloy about an inflatable body, and cooling 110 the stent to a temperature sufficient to obtain a martensitic phase of the shape memory alloy in at least a portion of the stent. The inflatable body is inflated 120 to radially expand the stent to an expanded diameter from an initial diameter, and then deflated 130. The expanded stent is positioned 140 over a mandrel sized to accommodate the expanded diameter of the stent, where the stent reaches a mandrel-defined diameter. The stent is then heat set 150 at the mandrel-defined diameter to impart a memory of an expanded configuration of the stent to the shape memory alloy.

Figure 2:
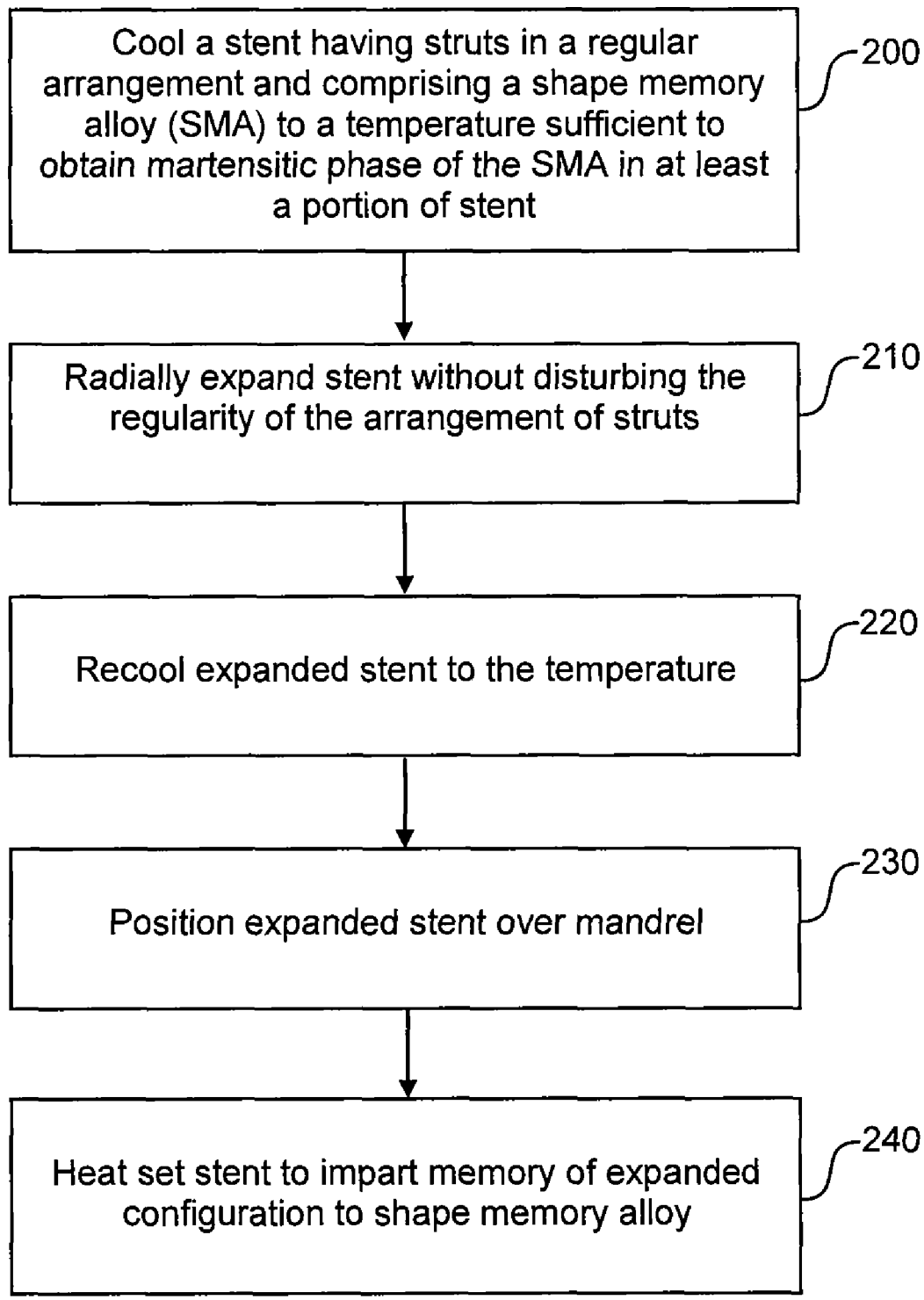
FIG. 2 is a flow chart of the method according to a second embodiment.

According to a second embodiment of the method represented in the flow chart of FIG. 2, a stent having struts in a regular arrangement and comprising a shape memory alloy is cooled 200 to a temperature sufficient to obtain a martensitic phase of the shape memory alloy in at least a portion of the stent. The stent is radially expanded 210 to an expanded diameter from an initial diameter without disturbing the regularity of the arrangement of the struts. The expanded stent is then recooled 220 to the temperature and positioned 230 over a mandrel sized to accommodate the expanded diameter of the stent, where the stent reaches a mandrel-defined diameter. The stent is then heat set 240 at the mandrel-defined diameter to impart a memory of an expanded configuration of the stent to the shape memory alloy.

Figure 3:
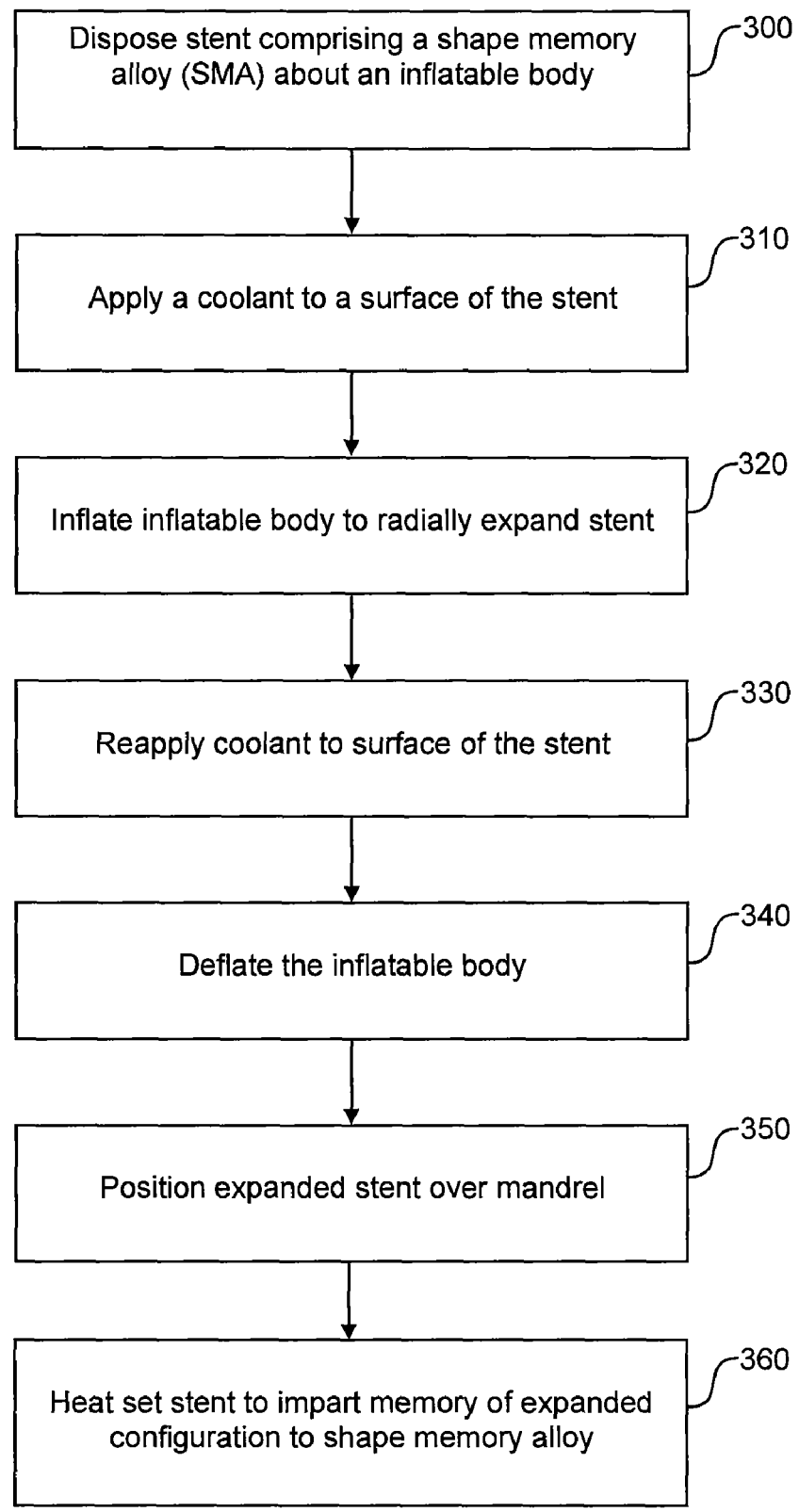
FIG. 3 is a flow chart of the method according to a third embodiment.

According to a third embodiment of the method represented in the flow chart of FIG. 3, a stent comprising a shape memory alloy is disposed 300 about an inflatable body, and a coolant is applied 310 to a surface of the stent. The inflatable body is inflated 320 to radially expand the stent to an expanded diameter from an initial diameter. The coolant is reapplied 330 to the surface of the stent, and the inflatable body is deflated 340. The stent is positioned 350 over a mandrel sized to accommodate the expanded diameter of the stent, where the stent reaches a mandrel-defined diameter. The stent is then heat set 360 at the mandrel-defined diameter to impart a memory of an expanded configuration of the stent to the shape memory alloy.

The shape memory alloy employed in the present method is preferably an equiatomic or near-equiatomic nickel-titanium alloy (e.g., Nitinol) that can be trained to "remember" and recover a previous shape. The source of the shape recovery in Nitinol alloys is a phase transformation between a lower temperature phase (martensite) and a higher temperature phase (austenite) that may be driven by an increase in temperature (shape memory effect) or by the removal of an applied stress (superelastic effect). Slightly nickel-rich Nitinol alloys including, for example, about 51 at. % Ni and about 49 at. % Ti are known to be useful for stents and other medical devices which behave superelastically at body temperature. More specifically, nickel-titanium alloys including 50.6-50.8 at. % Ni and 49.2-49.4 at. % Ti are considered to be medical grade Nitinol alloys and are suitable for the stent employed in the present method. The nickel-titanium alloy may also include one or more additional alloying elements that substitute for one or both of nickel and titanium.

The inflatable body that may be employed to radially expand the stent preferably extends along the length of the stent and inflates to a cylindrical configuration. The inflatable body may be made of a non-compliant or semi-compliant polymer, such as polyethylene terephthalate (PET). PET is believed to be particularly suitable for withstanding the cooling effected by application of a coolant to the surface of the stent. Other polymeric materials that may also be suitable for the inflatable body include Nylon and polyvinyl chloride (PVC). Medical balloons that are commercially available from Advanced Polymers, Inc. (Salem, N.H.) or other manufacturers may be used as the inflatable body.

Figure 4A:
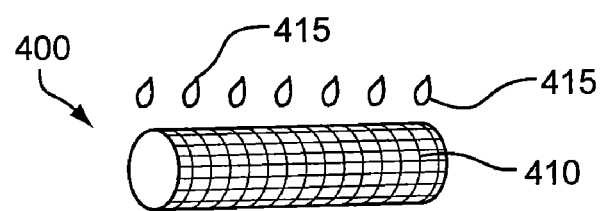
FIGS. 4A-4H depict the method schematically according to a preferred embodiment in which an inflatable body is employed to expand the stent.
Figure 4B:
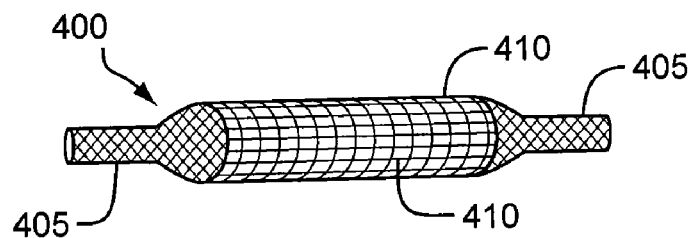

FIGS. 4A-4H depict the method schematically according to a preferred embodiment in which the radial expansion of the stent is carried out by inflating an inflatable body (e.g., a medical balloon) that underlies the stent. Referring first to FIG. 4B, a stent 400 having an initial, unexpanded diameter is disposed about an uninflated medical balloon 405. The stent 400 is preferably formed of a shape memory alloy, such as a nickel-titanium alloy as described above, and may include a regular arrangement of struts 410 formed by, for example, laser cutting a shape memory alloy tube. The regular arrangement of the struts 410 may have any pattern suitable for a stent, such as a z-pattern, w-pattern, ring pattern or other patterns known in the art. It may be advantageous, before disposing the stent 400 about the balloon 405, to cool the stent 400 to a temperature at which at least a portion of the shape memory alloy is martensitic, as discussed further below and as depicted in FIG. 4A. The cooled stent may then be slid over or otherwise positioned about the uninflated inflatable body, as shown in FIG. 4B. The balloon 405 preferably has a length at least as long as that of the stent 400.

Figure 4C:
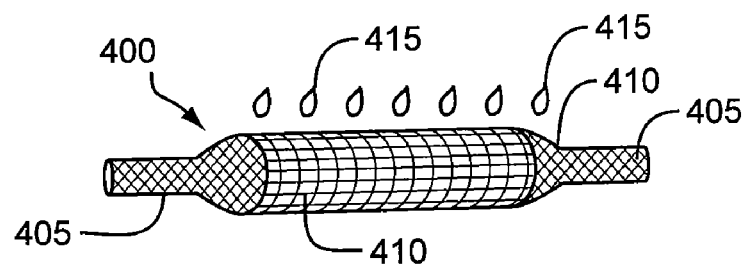

Referring to FIG. 4C, the stent 400 is preferably cooled before the balloon is inflated and the radial expansion is carried out. The cooling facilitates completely or partially transforming the shape memory alloy of the stent 400 to martensite, which can be more readily deformed than the high temperature austenitic phase of the alloy. The stent 400 is generally in position over the balloon 405 during the cooling step. Alternatively, the cooling of the stent 400 may occur immediately before the stent 400 is positioned over the balloon 405, and no additional cooling may occur before the stent 400 is expanded. The cooling generally occurs for a discrete time period, as described below, but it is also contemplated that the cooling may occur continuously as various steps of the method are carried out.

The cooling may entail applying a coolant 415 to a surface of the stent 400, as shown schematically in FIG. 4C. For example, Quik-Freeze®, a coolant 415 which is commercially available from Miller-Stephenson Chemical Company, Inc. (Danbury, Conn.), may be sprayed onto all or a portion of the surface of the stent. Quik-Freeze is reportedly capable of instantly freezing small areas to −55° F. (−48° C.). In practice, the coolant 415 is applied for a time sufficient for frost to appear on the surface. Preferably, application of the coolant 415 to the surface causes at least a portion of the shape memory alloy of the stent 400 to transform to martensite. For example, all or a portion of the stent 400 may reach a temperature at or below the martensite start temperature of the shape memory alloy. It may be even more advantageous for all or a portion of the stent 400 to reach a temperature at or below the martensite finish temperature of the shape memory alloy. As generally understood by those skilled in the art, the martensite start temperature ($M_s$) of a shape memory alloy is the temperature at which the phase transformation to martensite begins upon cooling, and the martensite finish temperature ($M_f$) is the temperature at which the phase transformation to martensite concludes upon cooling. The coolant 415 may be sprayed or otherwise applied (e.g., by dipping or coating) to the surface. Besides Quik-Freeze®, other suitable coolants 415 include, for example, isopropyl alcohol and dry ice, or nitrogen gas of a controlled temperature produced by running liquid nitrogen through a heat exhanger.

Instead of, or in addition to, applying coolant 415 to the surface of the stent 400, the method may be carried out in a controlled environment maintained at an appropriately low temperature to cool the stent. If the only source of cooling is the controlled environment, then it is preferred that the temperature of the environment be maintained sufficiently low to transform all or a portion of the shape memory alloy of the stent to martensite. For example, the controlled environment may be maintained at a temperature of $M_s$ or below (e.g., about −30° C. or lower), or a temperature of $M_f$ or below (e.g., about −80° C. or lower). Such cooling may be achieved within a refrigerated chamber or by, for example, flowing liquid nitrogen (−196° C.) or another cryogenic fluid through the controlled environment. If the controlled environment is employed to achieve cooling in addition to directly applying coolant to the surface of the stent, then higher controlled environment temperatures may be used. For example, it may be advantageous to maintain the controlled environment at a temperature slightly below the austenite start temperature ($A_s$) of the shape memory alloy (e.g., below about 15° C.-20° C.). At such a temperature, any warming of the stent that occurs after applying the coolant to the surface of the stent would not be sufficient to transform the martensite formed in the stent to austenite. In addition, such a temperature may be better suited to balloon inflation than extremely cold temperatures below $M_s$ or $M_f$, particularly if the balloon material cannot withstand or operate at these temperatures.

It is noted that the values of $A_s$, $M_s$ and $M_f$ mentioned above are intended to be exemplary and not limiting, as the actual values may vary for different shape memory alloys. Generally speaking, the transformation temperatures of a shape memory alloy depend on its processing history and composition (e.g., the ratio of Ni to Ti and the concentration of additional alloying elements, if present). Differential scanning calorimetry (DSC) is a standard test method that may be employed to characterize phase transformations in materials. The technique is widely used to identify $A_s$, $M_s$, $M_f$ and other phase transformation temperatures of nickel-titanium shape memory alloys, typically in accordance with ASTM Standard F 2004-05, "Standard Test Method for Transformation Temperature of Nickel-Titanium Alloys by Thermal Analysis," which is hereby incorporated by reference in its entirety.

Figure 4D:
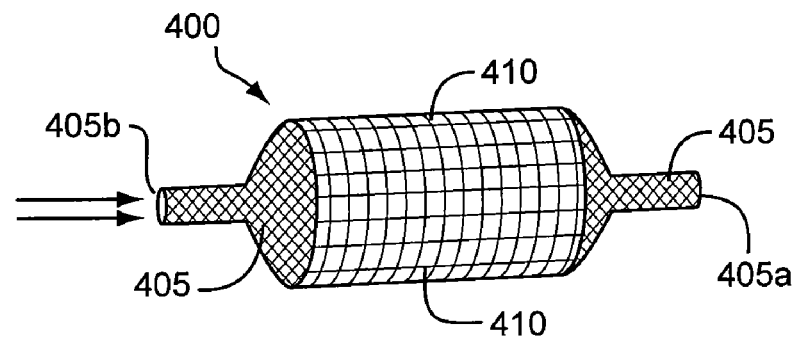

Referring now to FIG. 4D, the inflatable body or balloon 405 may be inflated to radially expand the stent 400 from an initial diameter to an expanded diameter by sealing off one end 405a of the deflated, collapsed balloon 405 and delivering an inflation fluid (gas or liquid) 420 into the other end 405b. The end of the balloon 405b that is not sealed may be flared, attached to a flared adapter and connected to a source of an inflation fluid, such as a compressed air line. Besides compressed air, suitable fluids 420 may include water, oil, alcohol, or other coolants. Once connected to the inflation fluid source, the balloon 405 is generally inflated to a pressure of from about 1.5 atm to about 10 atm to effect the expansion. For example, an inflation pressure of about 5 atm may be suitable. The inflation may be carried out in a matter of seconds, e.g., from about 1 second to about 20 seconds. It may be advantageous to do the expansion more gradually, such as over a time period of from about 10 seconds to about 20 seconds. The inflation preferably takes less than 60 seconds.

Preferably, for a stent 400 having a regular arrangement of struts 410 at the initial diameter, the radial expansion of the stent 400 does not substantially disturb or impair the regularity of the arrangement. It is believed that the regularity of the arrangement can be maintained by minimizing longitudinally directed stresses (e.g., frictional stresses) on the struts 410 during the radial expansion. To avoid such longitudinal stresses, the preferred means of radial expansion is balloon inflation; however, other mechanisms for expanding the stent 400 that do not result in strut misalignments may alternatively be employed. Thus, in the preferred method, the stent is uniformly expanded without moving the stent longitudinally during the expansion. As noted above, the balloon 405 preferably extends along the length of the stent 400 and inflates to a cylindrical configuration.

Figure 4E:
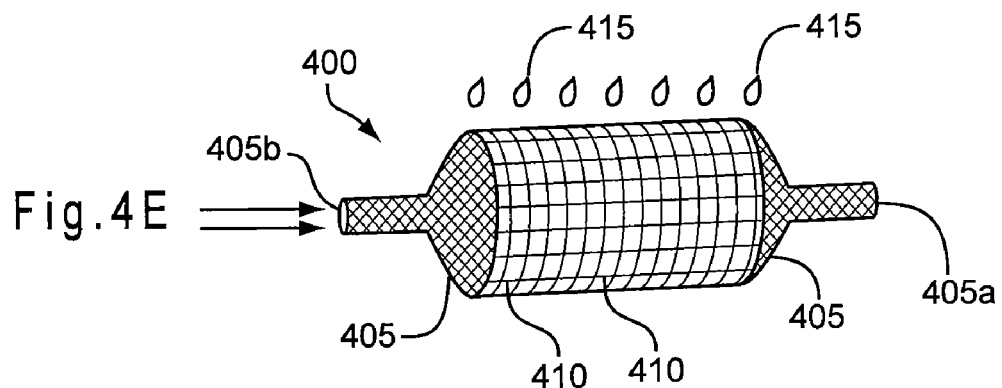
Figure 4F:
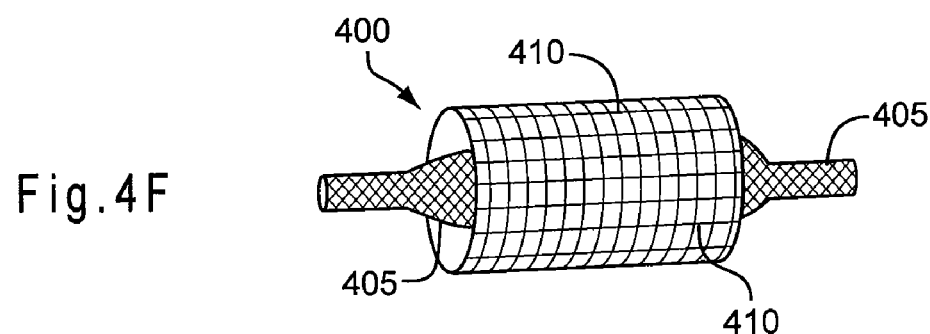
Figure 4G:
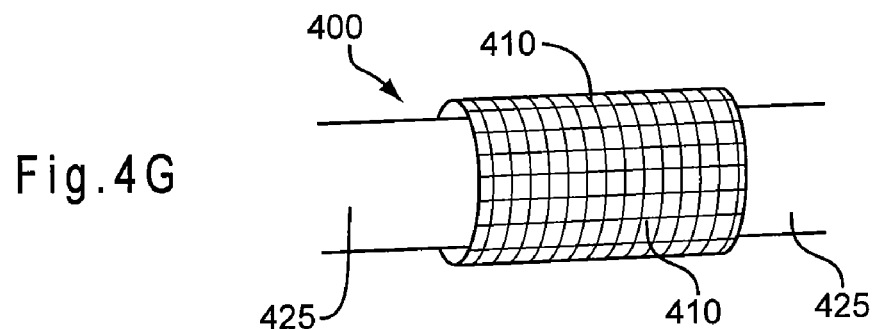

Referring to FIG. 4F, once the stent 400 has reached the expanded diameter, the balloon 405 is deflated, and the stent 400 may be transferred to a mandrel 425 having an outer diameter sized to accommodate the expanded stent 400, as shown in FIG. 4G. The stent 400 is preferably recooled before deflating the balloon 405 and positioning the stent 400 on the mandrel 425, as depicted in FIG. 4E. The recooling is particularly advantageous when the method is not carried out in a controlled environment maintained at a temperature sufficient to maintain a martensitic structure in the stent. The recooling ensures that the shape memory alloy of the stent 400 is least partly martensitic—and preferably fully martensitic—before the outward radial force exerted by the inflated balloon 405 is released. As noted above, the stent employed in the process may have an austenite start temperature ($A_s$) in the range of about 15° C.-20° C., such that a transformation to austenite may occur spontaneously if the stent is allowed to warm up to room temperature. (An austenitic stent will tend to return to the initial diameter when the radial force exerted by the balloon is released due to the shape memory effect, whereas a martensitic stent is expected to experience a minimal amount of recoil to the initial diameter.) The recooling of the stent 400 can be carried out as described above in reference to the cooling that occurs prior to the radial expansion.

Figure 4H:
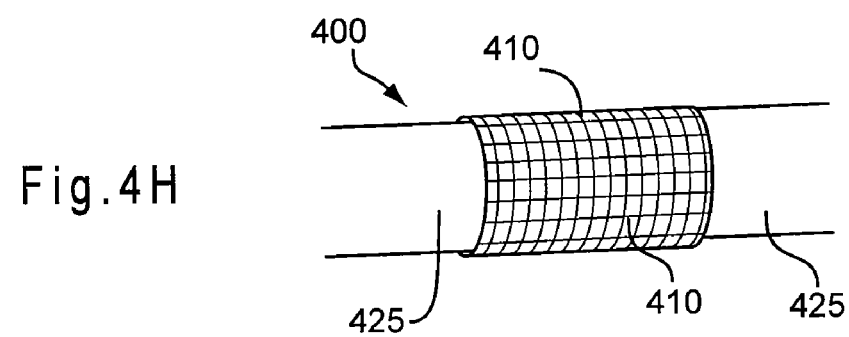

A suitable mandrel 425 may be any cylindrical body that can support the stent at the desired expanded diameter for heat setting. Preferably, the mandrel 425 is made of steel or another hard, heat-resistant metal alloy. Generally, the outer diameter of the mandrel 425 is slightly smaller than the inner diameter of the expanded stent 400, so that the stent 400 may be readily slid over the mandrel 425. Once positioned about the mandrel 425, and after warming up to an austenitic state, the stent 400 may recoil slightly to fit closely about the mandrel 425, thereby reaching a mandrel-defined diameter. Referring to FIG. 4H, the stent 400 is generally heat set at the mandrel-defined diameter so as to impart a memory of an expanded configuration to the shape memory alloy of the stent. The heat setting may be carried out by heating the stent to a temperature in the range of from about 350° C. to about 550° C., for example. As a consequence of the heat setting treatment, the stent attains the properties of a self-expanding stent that can automatically deploy to the expanded configuration at a treatment site in a body vessel.

The expansion of the stent to a desired final diameter may be achieved incrementally by carrying out the steps of the method (e.g., as shown schematically in FIGS. 4A-4H) more than one time. In other words, it may be advantageous for the disposing, cooling, expanding (e.g., inflating and deflating), positioning, and heat setting to be carried out two or more times in order to obtain the desired final diameter of the stent. For example, the initial diameter of the stent may be about 1.6 mm (outer diameter or OD) and the desired final diameter may be about 8 mm OD. After a first pass through the steps of the method, a first expanded diameter of the stent may be about 4 mm OD. The first expanded diameter of the stent is preferably at least about 100% larger, or at least about 150% larger, than the initial diameter. The first expanded diameter may also be at least about 200% larger than the initial diameter. It is generally preferred that the final diameter is at least about 400% larger than the initial diameter of the stent.

A new method of making a self-expanding stent has been described herein. The method allows a stent comprising a shape memory alloy to be radially expanded for a heat setting treatment without experiencing excessive longitudinal stresses or strut misalignments. Accordingly, the stent may undergo the heat setting treatment without first undergoing a tedious process of reorienting misaligned struts.

Although the present invention has been described in considerable detail with reference to certain embodiments thereof, other embodiments are possible without departing from the present invention. The spirit and scope of the appended claims should not be limited, therefore, to the description of the preferred embodiments contained herein.

All embodiments that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment.

The invention claimed is:

1. A method of making a self-expanding stent, the method comprising:
    disposing a stent comprising a shape memory alloy about an inflatable body;
    cooling the stent to a temperature sufficient to obtain a martensitic phase of the shape memory alloy in at least a portion of the stent;
    inflating the inflatable body to radially expand the stent to an expanded diameter from an initial diameter;
    deflating the inflatable body;
    positioning the stent about a mandrel sized to accommodate the expanded diameter of the stent, the stent reaching a mandrel-defined diameter; and
    heat setting the stent at the mandrel-defined diameter so as to impart a memory of an expanded configuration of the stent to the shape memory alloy.

2. The method of claim 1 further comprising recooling the stent to the temperature before deflating the inflatable body.

3. The method of claim 2 wherein cooling and recooling the stent to the temperature comprises applying a coolant to a surface of the stent.

4. The method of claim 1 wherein cooling the stent to the temperature comprises carrying out the method in a controlled environment maintained at the temperature.

5. The method of claim 1 wherein the temperature is at or below a martensite finish temperature of the shape memory alloy.

6. The method of claim 1 wherein the stent comprises a regular arrangement of struts at the initial diameter, and wherein inflating the inflatable body to radially expand the stent does not substantially disturb the regularity of the arrangement.

7. The method of claim 1 wherein the stent recoils to the mandrel-defined diameter.

8. The method of claim 1 wherein the mandrel-defined diameter is at least 150% larger than the initial diameter.

9. The method of claim 1 wherein heat setting the stent comprises heating the stent at a temperature in the range of from about 350° C. to about 550° C.

10. The method of claim 1 wherein the disposing, cooling, inflating, deflating, positioning, and heat setting are carried out more than one time to incrementally obtain a desired final diameter of the stent.

11. The method of claim 10 wherein the desired final diameter is at least 400% larger than the initial diameter of the stent.

12. The method of claim 1 wherein disposing the stent about the inflatable body comprises cooling the stent to the temperature and positioning the stent over the inflatable body.

13. A method of making a self-expanding stent, the method comprising:
    cooling a stent having struts in a regular arrangement and comprising a shape memory alloy to a temperature sufficient to obtain a martensitic phase of the shape memory alloy in at least a portion of the stent;
    radially expanding the stent to an expanded diameter from an initial diameter without substantially disturbing the regularity of the arrangement of the struts and without moving the stent longitudinally;
    recooling the stent having the expanded diameter to the temperature;
    positioning the stent about a mandrel sized to accommodate the expanded diameter of the stent, the stent reaching a mandrel-defined diameter; and
    heat setting the stent at the mandrel-defined diameter so as to impart a memory of an expanded configuration of the stent to the shape memory alloy.

14. The method of claim 13, wherein radially expanding the stent comprises uniformly radially expanding the stent along an entire length thereof.

15. The method of claim 13, wherein radially expanding the stent to the expanded diameter comprises inflating an inflatable body underlying the stent.

16. The method of claim 15, further comprising deflating the inflatable body after recooling the stent to the temperature and before positioning the stent about the mandrel.

17. The method of claim 13, wherein the cooling and recooling of the stent comprise applying and reapplying a coolant to a surface of the stent.

18. A method of making a self-expanding stent, the method comprising:
    disposing a stent comprising a shape memory alloy about an inflatable body;
    applying a coolant to a surface of the stent;
    inflating the inflatable body to radially expand the stent to an expanded diameter from an initial diameter;
    reapplying the coolant to the surface of the stent;
    deflating the inflatable body;
    positioning the stent about a mandrel sized to accommodate the expanded diameter of the stent, the stent reaching a mandrel-defined diameter; and
    heat setting the stent at the mandrel-defined diameter so as to impart a memory of an expanded configuration of the stent to the shape memory alloy.

19. The method of claim 18 wherein the applying and the reapplying of the coolant to the surface of the stent comprise spraying the coolant onto the surface for a time sufficient for frost to appear on the stent.

20. A method of making a self-expanding stent, the method comprising:
    cooling a stent having struts in a regular arrangement and comprising a shape memory alloy to a temperature sufficient to obtain a martensitic phase of the shape memory alloy in at least a portion of the stent;
    radially expanding the stent to an expanded diameter from an initial diameter without substantially disturbing the regularity of the arrangement of the struts;
    recooling the stent having the expanded diameter to the temperature;
    positioning the stent about a mandrel sized to accommodate the expanded diameter of the stent, the stent reaching a mandrel-defined diameter; and
    heat setting the stent at the mandrel-defined diameter so as to impart a memory of an expanded configuration of the stent to the shape memory alloy,
    wherein radially expanding the stent to the expanded diameter comprises inflating an inflatable body underlying the stent, and further comprising deflating the inflatable body after recooling the stent to the temperature and before positioning the stent about the mandrel.

* * * * *